United States Patent [19]

Kume et al.

[11] Patent Number: 4,675,331
[45] Date of Patent: Jun. 23, 1987

[54] ARTHROPODICIDAL BENZOTHIAZOLYL AND BENZOXAZOLYL BENZAMIDES

[75] Inventors: Toyohiko Kume; Shinichi Tsuboi; Kunihiro Isono; Shoko Sasaki; Yumi Hattori, all of Tokyo, Japan

[73] Assignee: Nihon Tokushu Noyaku Seizo K.K., Tokyo, Japan

[21] Appl. No.: 843,888

[22] Filed: Mar. 25, 1986

[30] Foreign Application Priority Data

Mar. 30, 1985 [JP] Japan .............................. 60-65018[U]

[51] Int. Cl.$^4$ ...................... A01N 43/78; A01N 43/76; C07D 277/82; C07D 263/58
[52] U.S. Cl. .................................... 514/367; 514/375; 548/163; 548/222
[58] Field of Search ............... 548/163, 222, 195, 233; 514/367, 377, 375, 371

[56] References Cited

FOREIGN PATENT DOCUMENTS 230416 3/1944 Switzerland ........................ 548/163

OTHER PUBLICATIONS

K. Kamala et al, Chemical Abstracts vol. 101, No. 110826k (1984).
G. Sarkas et al, Chemical Abstracts vol. 104, No. 207181w (1986).
J. Agric. Food Chem., Oliver et al, "Insect Growth Regulators, Analogues of TH-6038 and Th-6040", vol. 24, (1976) pp. 1065–1068.

Primary Examiner—Donald G. Daus
Assistant Examiner—Mary E. Ceperley
Attorney, Agent, or Firm—Sprung Horn Kramer & Woods

[57] ABSTRACT

Novel arthropodicidally active benzamides of the formula

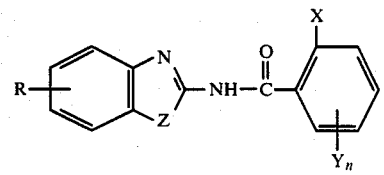

in which
X is a halogen atom, a lower alkyl group, a lower alkoxy group or a halogen-substituted lower alkyl group,
Y is a halogen atom or a lower alkyl group,
n is 0, 1 or 2,
Z is an oxygen or sulfur atom, and
R is a halogen-substituted lower alkyl group, a halogen-substituted lower alkoxy group, a halogen-substituted lower alkylthio group, a halogen-substituted lower alkylsulfinyl group of a halogen-substituted lower alkylsulfonyl group.

9 Claims, No Drawings

ARTHROPODICIDAL BENZOTHIAZOLYL AND BENZOXAZOLYL BENZAMIDES

This invention relates to novel benzamides, a process for production thereof, and use thereof as a pesticide, particularly insecticide.

It has been disclosed that certain benzamides, e.g. N-(6-chlorobenzothiazol-2-yl)-2,6-difluorobenzamide, have insecticidal activities (see J. Agric. Food Chem., Vol. 24, 1976, pages 1065–1068).

There have been found novel benzamides of the formula (I)

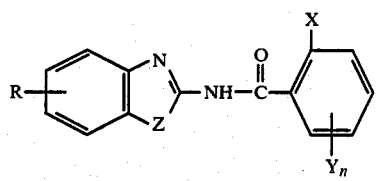

whereas X represents a halogen atom, a lower alkyl group, a lower alkoxy group or a halogen-substituted lower alkyl group, Y represents a halogen atom or a lower alkyl group, n represents 0, 1 or 2, Z represents an oxygen or sulfur atom, and R represents a halogen-substituted lower alkyl group, a halogen-substituted lower alkoxy group, a halogen-substituted lower alkylthio group, a halogen-substituted lower alkylsulfinyl group or a halogen-substituted lower alkylsulfonyl group.

The compounds of the formula (I) are obtained when the compounds of the formula (II)

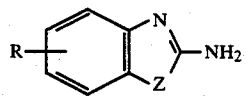

wherein Z and R are as defined, are reacted with the compounds of the formula (III)

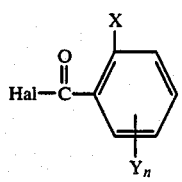

wherein X, Y and n are as defined and Hal represents a halogen atom, if appropriate, in the presence of inert solvents and in the presence of acid binders.

The novel benzamides exhibit excellent insecticidal activity.

Surprisingly, the benzamides according to the invention exhibit a substantially greater insecticidal action, in particular, against larvae of Lepidopterous insects, relative to analogues known from the aforesaid prior art.

The lower alkyl groups X and Y are straight-chain or branched and contain 1 to 8, preferably 1 to 6 and particularly preferably 1 to 4 carbon atoms. Examples which may be mentioned are methyl, ethyl, n- and i-propyl and n-, i-, s- and t-butyl. Preferred are methyl and ethyl, particularly preferred is methyl.

The lower alkoxy groups X are straight-chain or branched and contain 1 to 8, preferably 1 to 6 and particularly preferably 1 to 4 carbon atoms. Examples which may be mentioned are methoxy, ethoxy, n- and i-propoxy and n-, s-, i- and t-butoxy. Preferred are methoxy and ethoxy, particularly preferred is methoxy.

The halogen substituted lower alkyl groups X are straight-chain or branched and contain 1 to 8, preferably 1 to 6 and particularly preferably 1 to 4 carbon atoms and 1 to 7, preferably 1 to 5 and particularly preferably 1 to 3 (same or different) halogen atoms. Halogen atoms are fluorine, chlorine, bromine and iodine, preferably fluorine, chlorine and bromine, particularly preferably fluorine and chlorine. Examples which may be mentioned are $CHF_2$, $CF_3$, $CF_2CF_3$, $CH_2CF_3$ and $CF_2CHCl_2$, the $CF_3$ group being particularly preferred.

The lower alkyl groups in halogen-substituted lower alkyl, lower alkoxy, lower alkylthio, lower alkylsulfinyl or lower alkylsulfonyl R are straight-chain or branched and contain 1 to 8, particularly preferably 1 to 4 and more particularly preferably 1 or 2 carbon atoms. Examples which may be mentioned are methyl, ethyl, n- and i-propyl and n-, i-, s- and t-butyl. They can be substituted by 1 to 7, preferably 1 to 5 and particularly preferably 1 to 3 (same or different) halogen atoms. Preferred halogen atoms are fluorine, chlorine, bromine and iodine, particularly preferred are fluorine and chlorine. Examples which may be mentioned are $CF_3$, $CF_2CHCl_2$, $OCF_3$, $OCHF_2$, $OCF_2CHF_2$, $OCF_2CF_3$, $OCH_2CF_3$, $OCF_2CHCl_2$, $OCF_2CHFCF_3$, $SCHF_2$, $SCF_3$, $SCF_2CH_2F$, $SCF_2CF_3$, $SOCF_3$, $SOCH_2CF_3$, $SO_2CF_3$ and $SO_2CH_2CF_3$. Particularly preferred are $CF_3$, $OCF_3$ and $SCF_3$. Preferably R is in the 4-, 5- or 6-position, particularly preferably in the 6-position of the benzothiazol-2-yl or benzoxazol-2-yl radical.

In the general formulae (I) and (III) X and Y represent preferably halogen.

Halogen X and Y in formulae (I) and (III) means fluorine, chlorine, bromine or iodine, preferably fluorine, chlorine and bromine, particularly preferably fluorine and chlorine.

In the general formulae (I) and (II) Z preferably is sulfur.

n in general formulae (I) and (III) stands preferably for 0 or 1.

When n is 2, the substituents Y are preferably in the 2- and 4- or in the 4- and 6-positions of the benzoyl radical, and when n is 1, the substituent Y is preferably in the 4-, 5- or 6-position, particularly preferably in the 6-position of the benzoyl radical.

Preferred compounds of formula (I) are those, in which
 X represents halogen, $C_1$–$C_4$-alkyl, $C_1$–$C_4$-alkoxy, or halogen-$C_1$–$C_4$-alkyl (preferably halogen),
 Y represents halogen or $C_1$–$C_4$-alkyl (preferably halogen),
 n represents 0, 1 or 2 (preferably 0 or 1),
 Z represents oxygen or sulfur (preferably sulfur) and
 R represents a halogen (preferably fluoro and/or chloro) substituted radical from the group of $C_1$–$C_4$-alkyl, $C_1$–$C_4$-alkoxy, $C_1$–$C_4$-alkylthio, $C_1$–$C_4$-alkylsulfinyl and $C_1$–$C_4$-alkylsulfonyl (preferably $C_1$–$C_4$-alkyl, $C_1$–$C_4$-alkoxy and $C_1$–$C_4$-alkylthio).

Preferred compounds of formula (I) in accordance with this invention may be those in which X is chloro, fluoro, methyl, methoxy or trifluoromethyl, Y is chloro, fluoro or methyl, n is 0, 1 or 2, Z is a sulfur atom, and R is a fluoro-substituted alkyl group having 1 or 2 carbon atoms, a fluoro-substituted alkoxy group having 1 or 2 carbon atoms or a fluoro-substituted alkylthio group having 1 or 2 carbon atoms.

In the compounds of formula (I) having the above preferred definitions, especially preferred are those in which X is chloro or fluoro, Y is fluoro, n is 0 or 1, Z is a sulfur atom, and R is a trifluoromethyl or trifluoromethoxy group.

Moreover, in addition to the above preferred or especially preferred definitions, the most preferred compounds of the formula (I) are those in which R is substituted at the 6-position of the benzothiazole.

The following compounds can be particularly cited as specific examples of the compounds of the formula (I):
N-(6-trifluoromethylbenzothiazol-2-yl)-2,6-difluorobenzamide,. and
N-(6-trifluoromethoxybenzothiazol-2-yl)-2,6-difluorobenzamide.

When in the above process, 2-amino-6-trifluoromethylbenzothiazole and 2,6-difluorobenzoyl chloride, for example, are used as starting materials, the reaction can be shown by the following scheme:

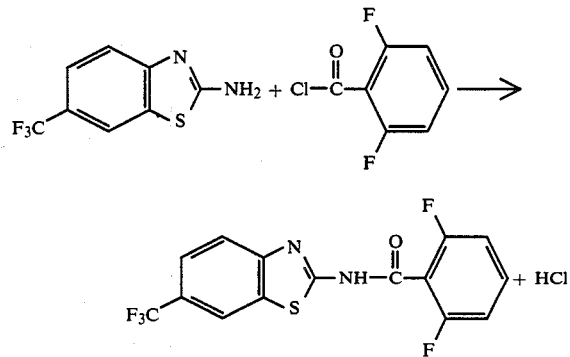

The compounds of the formula (II) are known (see, for example, U.S. Pat. No. 2,832,761, Zh. Obshch. Khim., Vol. 33 (7), 2301-7 (1963), and European Laid-Open Patent Publication No. 50,551).
Specific examples include
2-amino-6-trifluoromethylbenzothiazole,
2-amino-6-trifluoromethoxybenzothiazole,
2-amino-6-difluoromethoxybenzothiazole,
2-amino-6-(1,1,2,2-tetrafluoroethoxy)benzothiazole, and
2-amino-6-trifluoromethylthiobenzothiazole.

The compounds of the formula (II) exemplified above can be prepared from substituted anilines or substituted o-hydroxyanilines in accordance with methods known per se which are described, for example, in J. Chem. Soc., 1969, 268, Japanese Laid-Open Patent Publication No. 59,679/1984, West German Laid-Open Patent Publication No. 2,601,700, J. Pharm. Soc. Japan, Vol. 73 (1953), 1312, and J. Am. Chem. Soc., Vol. 71, 3417.

The compounds of formula (III) are known.
Specific examples include
2-chlorobenzoyl chloride,
2-chloro-6-fluorobenzoyl chloride,
2,6-difluorobenzoyl chloride,
2-fluorobenzoyl chloride,
2-methylbenzoyl chloride,
2-ethylbenzoyl chloride,
2-methoxybenzoyl chloride,
2,6-dichlorobenzoyl chloride,
2-trifluoromethylbenzoyl chloride,
2,4,6-trifluorobenzoyl chloride
and the corresponding bromides.

The above process can be performed in accordance with the known method described in U.S. Pat. No. 3,555,157.

In carrying out the above process, suitable diluents may be all inert solvents.

Examples of such diluents include aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acide amides such as dimethylformamide and dimethylacetamide; sulfones and sulfoxides such as dimethyl sulfoxide and sulfolane; and bases such as pyridine or 4-dimethylaminopyridine.

The above process can be carried out also in the presence of an acid binder. Examples of such an acid binder include organic tertiary amines such as triethylamine, dimethylaniline, pyridine and lutidine, and inorganic bases, for example alkali metal hydroxides and carbonates such as sodium hydroxide, potassium hydroxide, sodium carbonate and potassium carbonate.

The above process can be carried out over a wide temperature range, for example at a temperature between about −20° C. and the boiling point of the mixture, preferably between about 0° C. and about 150° C. Desirably, the reaction is carried out under normal atmospheric pressure, but it is also possible to operate under elevated or reduced pressures.

In the practice of the above process, the desired novel compounds of the formula (I) can be obtained by reacting 1 mole of the compound of general formula (II) with about 0.8 to about 1.2 moles, preferably 1 to about 1.1 moles, of the compound of general formula (III) in an inert solvent in the presence of an acid binder.

The active compounds of this invention represented by formula (I) exhibit strong pesticidal, preferably arthropodicidal and particularly preferably insecticidal activity, and therefore can be used as insecticides. The active compounds (I) of the invention show an accurate control effect on harmful insects without causing injury to cultivated plants. Furthermore, the compounds of this invention can be used for control and eradication of a wide range of pests, including sucking insects, biting insects and other plant parasites, pests on stored grains and pests causing health hazards.

Examples of the pests are shown below.

Coleopterous insects

*Callosobruchus chinensis,*
*Sitophilus zeamais,*
*Tribolium castaneum,*
*Epilachna vigitioctomaculata,*
*Agriotes fuscicollis,*
*Anomala rufocuprea,*
*Leptinotarsa decemkineata,*
Diabrotica spp.,
*Monochamus alternatus,*
*Lissorhoptrus oryzophilus,* and

*Lyctus brunneus.*

Lepidopterous insects

*Lymantria dispar,*
*Malacosoma neustria,*
*Pieris rapae,*
*Spodoptera litura,*
*Mamestra brassicae,*
*Chilo suppressalis,*
*Pyrausta nubilalis,*
*Ephestia cautella,*
*Adoxophyes orana,*
*Carpocapsa pomonella,*
*Agrotis fucosa,*
*Galleria mellonella,*
*Heliothis virescens,*
*Plutella maculipennis,* and
*Phyllocnistis citrella.*

Dipterous insects

*Musca domestica,*
*Aedes aegypti,*
*Hylemia platura,*
*Culex pipens,*
*Anopheles sinensis,* and
*Culex tritaeniorhynchus.*

In the field of animal farming and animal husbandry, the novel compounds of this invention are effective against various noxious animal parasites. Examples of such animal parasites are Gastrophilus spp. and Stomoxys spp.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents, diluents or carriers, there are suitable in the main, aromatic hydrocarbons, such as xylene, toluene or alkylnaphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formuations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms, etc.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The following examples illustrate the present invention specifically. It should be understood however that the invention is not to be limited to them alone.

PRODUCTION EXAMPLES

EXAMPLE 1

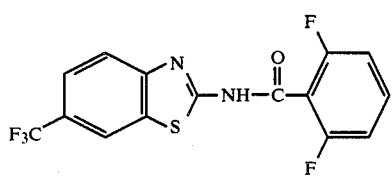

(compound No. 1)

At 0 to 5° C., 2,6-difluorobenzoyl chloride (1.77 g) was added dropwise to a solution composed of 2-amino-6-trifluoromethylbenzothiazole (2.18 g), tetrahydrofuran (30 ml) and triethylamine (1.1 g). The reaction mixture was stirred at 30 to 40° C. for 5 hours, and then tetrahydrofuran was evaporated. The solid residue was washed with water and recrystallized from ethanol to give the desired N-(6-trifluoromethylbenzothiazol-2-yl)-2,6-difluorobenzamide (2.8 g).

mp. 256°–257° C.

EXAMPLE 2

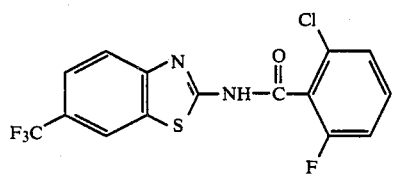

(compound No. 2)

At 0 to 5° C., 2-chloro-6-fluorobenzoyl chloride (1.93 g) was added dropwise to a solution composed of 2-amino-6-trifluoromethylbenzothiazole (2.18 g), pyridine (30 ml) and 4-dimethylaminopyridine (0.1 g). The reaction mixture was stirred at room temperature (20 to 30° C.) for one day, and then the pyridine was evaporated. Water was added to the residue, and the mixture was stirred. The resulting crystals were collected by filtration, and thoroughly washed with water. Recrystallization from ethanol gave the desired N-(6-trifluoromethylbenzothiazol-2-yl)-2-chloro-6-fluorobenzamide (2.5 g).

mp. 265°–270° C.

EXAMPLE 3

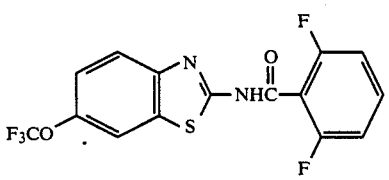

Compound No. 8

A mixture composed of 2-amino-6-trifluoromethoxybenzothiazole (2.34 g), 2,6-difluorobenzoylchloride (1.8 g) and chlorobenzene (20 ml) was boil for 1 hour. The hot reaction mixture was filtered and cooled to 10°–20° C. The resulting crystals were collected by filtration and washed with n-hexane (20 ml) to give N-(6-trifluoromethoxybenzothiazol-2-yl)-2,6-difluorobenzamide (3.15 g).

mp. 215°–216° C.

Table 1 below shows novel benzamides of general formula (I) in accordance with this invention synthesized by the same methods as in the above examples.

In Table 1, the indication "-" in the column headed by "$Y_n$" means that there is no substituent.

TABLE 1

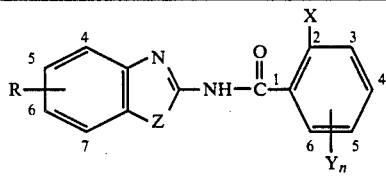

| Compound No. | R | Z | X | $Y_n$ | Physical Constant |
|---|---|---|---|---|---|
| 3 | 6-CF$_3$ | S | Cl | — | m.p. 225–226° C. |
| 4 | 4-CF$_3$ | S | F | 6-F | m.p. 215–216° C. |
| 5 | 5-CF$_3$ | S | F | 6-F | m.p. 214–216° C. |
| 6 | 6-CF$_3$ | O | F | 6-F | |
| 7 | 6-OCF$_3$ | S | Cl | — | m.p. 195–197° C. |
| 8 | 6-OCF$_3$ | S | F | 6-F | m.p. 215–216° C. |
| 9 | 6-SCF$_3$ | S | Cl | — | m.p. 206–207° C. |
| 10 | 6-SCF$_3$ | S | F | 6-F | m.p. 210–211° C. |
| 11 | 6-S(O)—CF$_3$ | S | F | 6-F | |
| 12 | 6-S(O)$_2$—CF$_3$ | S | F | 6-F | m.p. 208–210° C. |
| 13 | 6-SCH$_2$CF$_3$ | S | F | 6-F | m.p. 160–161° C. |
| 14 | 6-S(O)$_2$CH$_2$CF$_3$ | S | F | 6-F | |
| 15 | 6-OCHF$_2$ | S | F | 6-F | m.p. 196.5–197.5° C. |
| 16 | 6-OCF$_2$CHF$_2$ | S | F | 6-F | m.p. 210–211° C. |

TABLE 1-continued

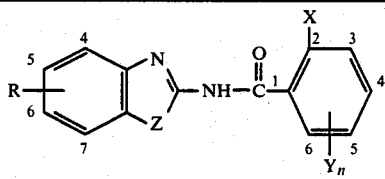

| Compound No. | R | Z | X | $Y_n$ | Physical Constant |
| --- | --- | --- | --- | --- | --- |
| 17 | 6-OCF$_2$CF$_3$ | S | F | 6-F | |
| 18 | 6-OCF$_2$CHCl$_2$ | S | F | 6-F | |
| 19 | 6-OCF$_2$CHFCF$_3$ | S | F | 6-F | m.p. 186–187° C. |
| 20 | 6-CF$_3$ | S | —CH$_3$ | — | m.p. 200–201° C. |
| 21 | 6-CF$_3$ | S | —C$_2$H$_5$ | — | |
| 22 | 6-CF$_3$ | S | F | — | m.p. 198–199° C. |
| 23 | 6-OCF$_3$ | S | Cl | 4-Cl | m.p. 211–211.5° C. |
| 24 | 6-CF$_3$ | S | F | 4,6-F$_2$ | |
| 25 | 6-OCF$_3$ | S | F | 6-CH$_3$ | |
| 26 | 6-OCF$_3$ | S | F | 4,6-F$_2$ | |
| 27 | 6-OCF$_3$ | S | Cl | 6-F | |
| 28 | 6-OCF$_3$ | O | Cl | 6-F | |
| 29 | 6-OCF$_3$ | S | —OCH$_3$ | — | m.p. 211–212° C. |
| 30 | 6-OCF$_3$ | S | Br | — | m.p. 208–209° C. |
| 31 | 6-OCF$_3$ | S | —CF$_3$ | — | m.p. 164–165° C. |
| 32 | 6-CF$_3$ | S | F | 6-Cl | m.p. 265–270° C. |
| 33 | 6-OCF$_2$CHF$_2$CF$_3$ | S | Cl | — | m.p. 167–169° C. |

USE EXAMPLES

Comparative compound A:

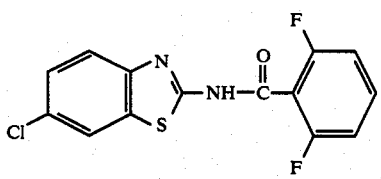

(the compound described in J. Agric. Food Chem., Vol. 24, 1976, pages 1065–1068)

EXAMPLE 3

Test on larvae of *Spodoptera litura*:
Preparation of a test chemical
Solvent: 3 parts by weight of dimethylformamide
Emulsifier: 1 part by weight of polyoxyethylene alkyl phenyl ether To make a suitable preparation of an active compound, 1 part by weight of the active compound was mixed with the emulsifier and the solvent in the above-indicated amounts. The mixture was diluted with water to a predetermined concentration.
Testing method Cabbage leaves were immersed in a water dilution of the active compound in a predetermined concentration. After air drying the chemical, the cabbage leaves were put in a Petri dish with a diameter of 9 cm. Five 3rd-instar larvae of *Spodoptera litura* were released into the Petri dish and the dish was placed in a constant-temperature chamber kept at 28° C. The kill ratio was calculated 7 days later.

The results obtained with typical compounds are shown in Table 2.

TABLE 2

| Compound No. | Concentration of the active ingredient (ppm) | Kill ratio (%) |
| --- | --- | --- |
| 1 | 2 | 100 |
| 2 | 10 | 100 |
| 3 | 10 | 100 |
| 8 | 2 | 100 |
| 10 | 10 | 100 |
| Comparison A | 40 | 80 |
| | 10 | 0 |

EXAMPLE 4

Test on larvae of *Plutella maculipennis*:
Testing method

Cabbage leaves were immersed in a water dilution of the active compound in a predetermined concentration prepared as in Example 3. After air drying the chemical, the cabbage leaves were put in a Petri dish having a diameter of 9 cm. Ten larvae of *Plutella maculipennis* were released into the dish, and the dish was placed in a constant-temperature chamber kept at 23° C. Seven days later, the kill ratio was calculated.

The results obtained with typical examples are shown in Table 3.

TABLE 3

| Compound No. | Concentration of the active ingredient (ppm) | Kill ratio (%) |
| --- | --- | --- |
| 1 | 10 | 100 |
| 2 | 40 | 100 |
| 3 | 40 | 100 |
| 7 | 10 | 100 |
| 8 | 2 | 100 |
| Comparison A | 200 | 100 |
| | 40 | 0 |

It will be understood that the specification and examples are illustrative but not limitative of the present invention and that other embodiments within the spirit and scope of the invention will suggest themselves to those skilled in the art.

What is claimed:

1. A benzamide of the formula

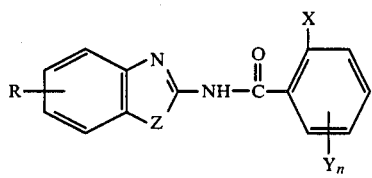

in which
- X is a halogen atom, a $C_{1-8}$ alkyl group, a $C_{1-8}$ alkoxy group or a halogen-substituted $C_{1-8}$ alkyl group,
- Y is a halogen atom or a $C_{1-8}$ alkyl group,
- n is 0, 1 or 2,
- Z is an oxygen or sulfur atom, and
- R is a halogen-substituted $C_{1-8}$ alkyl group, a halogen-substituted $C_{1-8}$ alkoxy group, a halogen-substituted $C_{1-8}$ alkylthio group, a halogen-substituted $C_{1-8}$ alkylsulfinyl group or a halogen-substituted $C_{1-8}$ alkylsulfonyl group.

2. A compound according to claim 1, in which
- X is halogen, $C_1$–$C_4$-alkyl, $C_1$–$C_4$-alkoxy, or halogen-$C_1$–$C_4$-alkyl,
- Y is halogen or $C_1$–$C_4$-alkyl, and
- R is halogen-substituted $C_1$–$C_4$-alkyl, $C_{1-4}$-alkoxy, $C_1$–$C_4$-alkylthio, $C_1$–$C_4$ -alkylsulfinyl or $C_1$–$C_4$-alkylsulfonyl.

3. A compound according to claim 1, in which
- X is chloro, fluoro, methyl, methoxy or trifluoromethyl,
- Y is chloro, fluoro or methyl,
- Z is a sulfur atom, and
- R is a fluoro-substituted alkyl group having 1 or 2 carbon atoms, a fluoro-substituted alkoxy group having 1 or 2 carbon atoms or a fluoro-substituted alkylthio group having 1 or 2 carbon atoms.

4. A compound according to claim 1, in which
- X is chloro or fluoro,
- Y is fluoro,
- n is 0 or 1,
- Z is a sulfur atom, and
- R is a trifluoromethyl or trifluoromethoxy group.

5. A compound according to claim 1, where such compound is N-(6-trifluoromethylbenzothiazol-2-yl)-2,6-difluorobenzamide of the formula

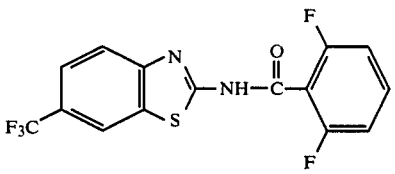

6. A compound according to claim 1, where such compound is N-(6-trifluoromethoxybenzothiazol-2-yl)-2,6-difluorobenzamide of the formula

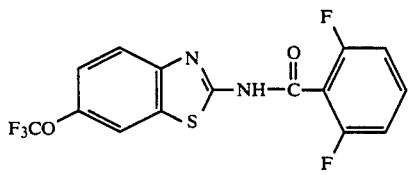

7. An arthropodicidal composition comprising an arthropodicidally effective amount of a compound according to claim 1 in admixture with a diluent.

8. A method of combatting arthropods which comprises applying thereto or to a habitat thereof an arthropodicidally effective amount of a compound according to claim 1.

9. The method according to claim 8, wherein such compound is
- N-(6-trifluoromethylbenzothiazol-2-yl)-2,6-difluorobenzamide or
- N-(6-trifluoromethoxybenzothiazol-2-yl)-2,6-difluorobenzamide.

* * * * *